(12) United States Patent
Gundlach et al.

(10) Patent No.: US 10,017,814 B2
(45) Date of Patent: Jul. 10, 2018

(54) SELECTIVE MODIFICATION OF POLYMER SUBUNITS TO IMPROVE NANOPORE-BASED ANALYSIS

(71) Applicants: University of Washington through its Center for Commercialization, Seattle, WA (US); Illumina, Inc., San Diego, CA (US)

(72) Inventors: Jens H. Gundlach, Seattle, WA (US); Andrew Laszlo, Seattle, WA (US); Ian Derrington, Seattle, WA (US); Jeffrey G. Mandell, La Jolla, CA (US)

(73) Assignees: University of Washington through its Center for Commercialization, Seattle, WA (US); Illumina, Inc., San Diego, CA (US)

( * ) Notice: Subject to any disclaimer, the term of this patent is extended or adjusted under 35 U.S.C. 154(b) by 185 days.

(21) Appl. No.: 14/915,611

(22) PCT Filed: Sep. 2, 2014

(86) PCT No.: PCT/US2014/053754
§ 371 (c)(1),
(2) Date: Feb. 29, 2016

(87) PCT Pub. No.: WO2015/031909
PCT Pub. Date: Mar. 5, 2015

(65) Prior Publication Data
US 2016/0222444 A1 Aug. 4, 2016

Related U.S. Application Data

(60) Provisional application No. 61/872,406, filed on Aug. 30, 2013.

(51) Int. Cl.
| *C12Q 1/68* | (2018.01) |
|---|---|
| *C12Q 1/6869* | (2018.01) |
| *B01D 57/02* | (2006.01) |
| *G01N 33/487* | (2006.01) |

(52) U.S. Cl.
CPC .......... *C12Q 1/6869* (2013.01); *B01D 57/02* (2013.01); *G01N 33/48721* (2013.01)

(58) Field of Classification Search
None
See application file for complete search history.

(56) References Cited

U.S. PATENT DOCUMENTS

| 2003/0134290 A1 | 7/2003 | Stanton, Jr. et al. | |
|---|---|---|---|
| 2005/0202444 A1 | 9/2005 | Zhu | |
| 2007/0117114 A1 | 5/2007 | Rashtchian et al. | |
| 2008/0260743 A1 | 10/2008 | Rehli | |
| 2009/0298072 A1* | 12/2009 | Ju | C12Q 1/6869 435/6.16 |
| 2010/0221716 A1* | 9/2010 | Flusberg | C12Q 1/6858 435/6.18 |
| 2011/0124518 A1* | 5/2011 | Cantor | C12Q 1/6816 506/9 |
| 2012/0091005 A1* | 4/2012 | Burrows | B82Y 15/00 204/605 |
| 2012/0160681 A1* | 6/2012 | Davis | G01N 33/48721 204/452 |
| 2013/0240359 A1* | 9/2013 | Turner | G01N 27/447 204/451 |
| 2013/0244885 A1 | 9/2013 | Wang et al. | |
| 2013/0264207 A1* | 10/2013 | Ju | C12Q 1/6869 204/452 |
| 2013/0327644 A1* | 12/2013 | Turner | C12Q 1/6869 204/543 |
| 2017/0096704 A1* | 4/2017 | Ju | C12Q 1/6869 |

FOREIGN PATENT DOCUMENTS

| CN | 1667401 A | 9/2005 |
|---|---|---|
| CN | 102046787 A | 5/2011 |
| EP | 2 281 883 A1 | 2/2011 |
| JP | 2007-507203 A | 3/2007 |
| WO | 2012/019320 A1 | 2/2012 |
| WO | 2013/090588 A1 | 6/2013 |

OTHER PUBLICATIONS

Notification of the First Office Action, dated Jul. 11, 2017, issued in corresponding Chinese Application No. 201480047714.6, filed Sep. 2, 2014, 37 pages.
Anderson, B.N., et al., "pH Tuning of DNA Translocation Time Through Organically Functionalized Nanopores," ACS Nano 7(2):1408-1414, Feb. 2013.
Ayub, M., and H. Bayley, "Individual RNA Base Recognition in Immobilized Oligonucleotides Using a Protein Nanopore," Nano Letters 12(11):5637-5643, Nov. 2012.
Clarke, J., et al., "Continuous Base Identification for Single-Molecule Nanopore DNA Sequencing," Nature Manotechnology 4(4):265-270, Apr. 2009.
Extended European Search Report dated Jun. 6,2017, issued in corresponding European Application No. 14841122.6, filed Sep. 2,2014, 7 pages.
Wolna, A.H., et al., "Electrical Current Signatures of DNA Base Modifications in Single Molecules Immobilized in the α-Hemolysin Ion Channel," Israel Journal of Chemistry 53(6-7):417-430, Jun. 2013. (Author Manuscript provided, PMCID: PMC3773884, available in PMC Jun. 1, 2014, 27 pages.).
International Search Report and Written Opinion dated Dec. 4, 2014, issued in corresponding International Application No. PCT/US2014/053754, filed Sep. 2, 2014, 11 pages.

(Continued)

*Primary Examiner* — Aaron A Priest
(74) *Attorney, Agent, or Firm* — Christensen O'Connor Johnson Kindness PLLC

(57) ABSTRACT

The present disclosure provides method and systems for improving nanopore-based analysis of polymers. The disclosure provides methods for selectively modifying one or more monomeric subunit(s) of a kind a pre-analyte polymer that results polymer analyte with a modified subunit. The polymer analyte produces a detectable signal in a nanopore-based system. The detectable signal, and/or its deviation from a reference signal, indicates the location of the modified subunit in the polymer analyte and, thus, permits the identification of the subunit at that location in the original pre-analyte polymer.

18 Claims, 3 Drawing Sheets

(56) References Cited

OTHER PUBLICATIONS

Laszlo, A. H., et al., "Detection and Mapping of 5-Methylcytosine and 5-Hydroxymethylcytosine With Nanopore MspA," PNAS 110(47):18904-18909, Nov. 2013.
Manrao, E. A., et al., "Reading DNA at Single-Nucleotide Resolution With a Mutant MspA Nanopore and Phi29 DNA Polymerase," Nature Biotechnology 30(4):349-353, Apr. 2012.
O'Connor, T. R., "Purification and Characterization of Human 3-Methyl-adenine-DNA Glycosylase," Nucleic Acids Research 21(24):5561-5569, Dec. 1993.
Wallace, E. V. B., et al., "Identification of Epigenetic DNA Modifications With a Protein Nanopore," Chemistry Communications (Cambridge) 46(43):8195-8197, Nov. 2010.
Zhu, B. et al. "Overexpression of 5-Methylcytosine DNA Glycosylase in Human Embryonic Kidney Cells EcR293 Demethylates the Promoter of a Hormone-Regulated Reporter Gene," PNAS 98(9):5031-5036, Apr. 2001.
Communication Pursuant to Article 94(3) EPC dated Feb. 15, 2018, issued in corresponding European Application No. 14841122.6, filed Sep. 2, 2014, 4 pages.
Examination Report No. 1 dated Feb. 23, 2018, issued in corresponding Australian Application No. 2014312020, filed Sep. 2, 2014, 4 pages.
Notification of the Second Office Action, dated Mar. 26, 2018, issued in corresponding Chinese Application No. 201480047714.6, filed Sep. 2, 2014, 24 pages.

\* cited by examiner

SEQUENCE LISTING

```
<160> NUMBER OF SEQ ID NOS: 9

<210> SEQ ID NO 1
<211> LENGTH: 14
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Wherein the N at position 14 is an abasic site

<400> SEQUENCE: 1
aaaaaaacct tccn                                                          14

<210> SEQ ID NO 2
<211> LENGTH: 44
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (37)..(43)
<223> OTHER INFORMATION: Wherein the N at positions 37 to 43 is an
      abasic site
<220> FEATURE:
<221> NAME/KEY: misc_feature
<222> LOCATION: (44)..(44)
<223> OTHER INFORMATION: Wherein the N at position 44 is a 3 carbon
      spacer

<400> SEQUENCE: 2
ttttattagt tgcttgattt acgatacgaa acgaaannnn nnnn                         44

<210> SEQ ID NO 3
```

```
<211> LENGTH: 92
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(92)
<223> OTHER INFORMATION: DNA/RNA Hybrid
<220> FEATURE:
<221> NAME/KEY: misc_feature
<222> LOCATION: (14)..(14)
<223> OTHER INFORMATION: Wherein the N at posistion 14 is an abasic site
<220> FEATURE:
<221> NAME/KEY: misc_feature
<222> LOCATION: (17)..(17)
<223> OTHER INFORMATION: Wherein the N at position 17 is a 5-methyl-C
<220> FEATURE:
<221> NAME/KEY: misc_feature
<222> LOCATION: (22)..(22)
<223> OTHER INFORMATION: Wherein the N at position 22 is a 5-methyl-C
<220> FEATURE:
<221> NAME/KEY: misc_feature
<222> LOCATION: (27)..(27)
<223> OTHER INFORMATION: Wherein the N at position 27 is a 5-methyl-C
<220> FEATURE:
<221> NAME/KEY: misc_feature
<222> LOCATION: (32)..(32)
<223> OTHER INFORMATION: Wherein the N at position 32 is a 5-methyl-C
<220> FEATURE:
<221> NAME/KEY: misc_feature
<222> LOCATION: (42)..(42)
<223> OTHER INFORMATION: Wherein the N at position 42 is a
    5-hydroxymethyl-C
<220> FEATURE:
<221> NAME/KEY: misc_feature
<222> LOCATION: (47)..(47)
<223> OTHER INFORMATION: Wherein the N at position 47 is a
    5-hydroxymethyl-C

<400> SEQUENCE: 3
aaaaaaacct tccnuungta ungtgungta ungttuugtt ungtaungta aatcaagcaa      60
ctaataaaag cattctcatg caggtcgtag cc                                   92

<210> SEQ ID NO 4
<211> LENGTH: 55
<212> TYPE: DNA
<213> ORGANISM: Artificial sequence
<220> FEATURE:
<223> OTHER INFORMATION: Synthetic

<400> SEQUENCE: 4
gcgtacgcct acggttttcc gtaggcgtac gcggctacga cctgcatgag aatgc          55

<210> SEQ ID NO 5
<211> LENGTH: 92
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Wherein the N at position 14 is an abasic site
<220> FEATURE:
<221> NAME/KEY: misc_feature
<222> LOCATION: (17)..(17)
<223> OTHER INFORMATION: Wherein the N at position 17 is a 5-methyl-C
<220> FEATURE:
<221> NAME/KEY: misc_feature
<222> LOCATION: (22)..(22)
<223> OTHER INFORMATION: Wherein the N at position 22 is a 5-methyl-C
<220> FEATURE:
<221> NAME/KEY: misc_feature
```

```
<222> LOCATION: (27)..(27)
<223> OTHER INFORMATION: Wherein the N at position 27 is a 5-methyl-C
<220> FEATURE:
<221> NAME/KEY: misc_feature
<222> LOCATION: (32)..(32)
<223> OTHER INFORMATION: Wherein the N at position 32 is a 5-methyl-C
<220> FEATURE:
<221> NAME/KEY: misc_feature
<222> LOCATION: (42)..(42)
<223> OTHER INFORMATION: Wherein the N at position 42 is a
      5-hydroxymethyl-C
<220> FEATURE:
<221> NAME/KEY: misc_feature
<222> LOCATION: (47)..(47)
<223> OTHER INFORMATION: Wherein the N at position 47 is a
      5-hydroxymethyl-C

<400> SEQUENCE: 5
aaaaaaacct tccnccngta cngtgcngta cngttccgtt cngtacngta aatcaagcaa        60
ctaataaaag cattctcatg caggtcgtag cc                                     92

<210> SEQ ID NO 6
<211> LENGTH: 42
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Wherein the N at position 14 is an abasic site

<400> SEQUENCE: 6
aaaaaaacct tccnacaccg attctcccga gtcggccgaa tc                          42

<210> SEQ ID NO 7
<211> LENGTH: 42
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(42)
<223> OTHER INFORMATION: DNA/RNA Hybrid
<220> FEATURE:
<221> NAME/KEY: misc_feature
<222> LOCATION: (14)..(14)
<223> OTHER INFORMATION: Wherein the N at position 14 is an abasic site

<400> SEQUENCE: 7
aaaaaaauut tuunauauug attutuuuga gtugguugaa tu                          42

<210> SEQ ID NO 8
<211> LENGTH: 45
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(45)
<223> OTHER INFORMATION: DNA/RNA Hybrid
<220> FEATURE:
<221> NAME/KEY: misc_feature
<222> LOCATION: (8)..(8)
<223> OTHER INFORMATION: Wherein the N at position 8 is an abasic site
<220> FEATURE:
<221> NAME/KEY: misc_feature
<222> LOCATION: (16)..(16)
<223> OTHER INFORMATION: Wherein the N at position 16 is a
      5-hydroxymethyl-C
```

```
<220> FEATURE:
<221> NAME/KEY: misc_feature
<222> LOCATION: (21)..(21)
<223> OTHER INFORMATION: Wherein the N at position 21 is a
      5-hydroxymethyl-C
<220> FEATURE:
<221> NAME/KEY: misc_feature
<222> LOCATION: (26)..(26)
<223> OTHER INFORMATION: Wherein the N at position 26 is a
      5-hydroxymethyl-C
<220> FEATURE:
<221> NAME/KEY: misc_feature
<222> LOCATION: (36)..(36)
<223> OTHER INFORMATION: Wherein the N at position 36 is a 5-methyl-C
<220> FEATURE:
<221> NAME/KEY: misc_feature
<222> LOCATION: (41)..(41)
<223> OTHER INFORMATION: Wherein the N at position 41 is a 5-methyl-C

<400> SEQUENCE: 8
accttccnuu cgtaungtgu ngtaungttu ugttungtau ngtaa                45

<210> SEQ ID NO 9
<211> LENGTH: 45
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Wherein the N at position 8 is an abasic site
<220> FEATURE:
<221> NAME/KEY: misc_feature
<222> LOCATION: (11)..(11)
<223> OTHER INFORMATION: Wherein the N at position 11is a
      5-hydroxymethyl-C
<220> FEATURE:
<221> NAME/KEY: misc_feature
<222> LOCATION: (16)..(16)
<223> OTHER INFORMATION: Wherein the N at position 16 is a
      5-hydroxymethyl-C
<220> FEATURE:
<221> NAME/KEY: misc_feature
<222> LOCATION: (21)..(21)
<223> OTHER INFORMATION: Wherein the N at position 21 is a
      5-hydroxymethyl-C
<220> FEATURE:
<221> NAME/KEY: misc_feature
<222> LOCATION: (26)..(26)
<223> OTHER INFORMATION: Wherein the N at position 26 is a
      5-hydroxymethyl-C
<220> FEATURE:
<221> NAME/KEY: misc_feature
<222> LOCATION: (36)..(36)
<223> OTHER INFORMATION: Wherein the N at position 36 is a 5-methyl-C
<220> FEATURE:
<221> NAME/KEY: misc_feature
<222> LOCATION: (41)..(41)
<223> OTHER INFORMATION: Wherein the N at position 41 is a 5-methyl-C

<400> SEQUENCE: 9
accttccncc ngtacngtgc ngtacngttc cgttcngtac ngtaa                45
```

SELECTIVE MODIFICATION OF POLYMER SUBUNITS TO IMPROVE NANOPORE-BASED ANALYSIS

CROSS-REFERENCE(S) TO RELATED APPLICATION(S)

This application claims the benefit of U.S. Application No. 61/872,406, filed Aug. 30, 2012.

STATEMENT OF GOVERNMENT LICENSE RIGHTS

This invention was made with government support under Grant No. R01HG005115, awarded by the National Institutes of Health. The government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 52586_SEQ_LISTING_ST25.txt. The text file is 6 KB; was created on Sep. 2, 2014; and is being submitted via EFS-Web with the filing of the specification.

BACKGROUND

The rapid, reliable, and cost-effective analysis of polymer molecules, such as sequencing of nucleic acids and polypeptides, is a major goal of researchers and medical practitioners. The ability to determine the sequence of polymers, such as a nucleic acid sequence in DNA or RNA or polypeptides, has additional importance in identifying genetic mutations and polymorphisms. Established DNA sequencing technologies have considerably improved in the past decade but still require substantial amounts of DNA and several lengthy steps and struggle to yield contiguous read-lengths of greater than 100 nucleotides. This information must then be assembled "shotgun" style, an effort that depends non-linearly on the size of the genome and on the length of the fragments from which the full genome is constructed. These steps are expensive and time-consuming, especially when sequencing mammalian genomes.

Nanopore-based analysis methods have been investigated as an alternative to traditional polymer analysis approaches. These methods involve passing a polymeric molecule, for example single-stranded DNA ("ssDNA"), through a nanoscopic opening while monitoring a signal, such as an electrical signal, that is influenced by the physical properties of the polymer subunits as the polymer analyte passes through the nanopore opening. The nanopore optimally has a size or three-dimensional configuration that allows the polymer to pass only in a sequential, single file order. Under theoretically optimal conditions, the polymer molecule passes through the nanopore at a rate such that the passage of each discrete monomeric subunit of the polymer can be correlated with the monitored signal. Differences in the chemical and physical properties of each monomeric subunit that makes up the polymer, for example, the nucleotides that compose a ssDNA, result in characteristic electrical signals that can identify each monomeric subunit as it passes through the nanopore. Nanopores, such as for example, protein nanopores held within lipid bilayer membranes and solid state nanopores, which have been heretofore used for analysis of DNA, RNA, and polypeptides, thus provide the potential advantage of robust analysis of polymers even at low copy number.

However, challenges remain for the full realization of such benefits. For example, in ideal sequencing conditions, the passage of each potential monomeric subunit-type through the nanopore would cause a distinct detectable signal that can be readily differentiated from detectable signals caused by the passage of any other monomeric subunit-types through the nanopore. However, depending on the structural characteristics of the nanopore and the particular polymer analyte, multiple monomeric subunit types can often produce detectable signals that are difficult to distinguish. For example, in the analysis of ssDNA using a protein nanopore based on *Mycobacterium smegmatis* porin A (MspA), the nucleotides in the constricted portion of the pore have the most influence on the ion current that flows through the pore. When monitoring the ion current, it has been found that the nucleotide residue adenine (A) results in the largest detectable current, whereas the residue thymine (T) results in the lowest detectable current. While the A and T residues can be readily distinguished, the nucleotide residues cytosine (C) and guanine (G) cause current levels that are similarly between the current levels caused by A and T residues. Accordingly, C and G residues are often difficult to distinguish from each other. In another example, analysis of ssDNA in the protein pore α-hemolysin results in signals that are even more compressed where there is signal overlap for all four nucleotide residues types, which makes base-calling uncertain.

Accordingly, a need remains to facilitate production of consistent, clear, and distinguishable signals that can differentiate each potential subunit type of a polymer. The methods and compositions of the present disclosure address this and related needs of the art.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a method for analyzing a polymer analyte. The method comprises:

(a) translocating a polymer analyte comprising a modified subunit from a first conductive liquid medium to a second conductive liquid medium through a nanopore, wherein the nanopore provides liquid communication between the first conductive liquid medium and the second conductive liquid medium;

(b) measuring an ion current between the first conductive liquid medium and the second conductive liquid medium as the polymer analyte passes through the nanopore; and (c) detecting the modified subunit based on the measured ion current.

In some embodiments, the method further comprises selectively modifying a target polymer subunit of a kind in a pre-analyte polymer prior to step (a), thereby producing the polymer analyte comprising a modified subunit. In some embodiments, modifying the target polymer subunit of a kind comprises contacting the pre-analyte polymer with an agent, wherein the agent is capable of selectively modifying the target polymer subunit of a kind in the pre-analyte polymer. In some embodiments, the pre-analyte polymer comprises a nucleic acid, a PNA, a polypeptide, or a combination thereof. In some embodiments, the nucleic acid is DNA or RNA. In some embodiments, the kind of target polymer subunit is a cytosine residue, a guanine residue, a thymine residue, an adenine residue, or a uracil residue.

In some embodiments, modifying the target polymer subunit of a kind comprises selectively converting the target polymer subunit of a kind into an abasic site. In some embodiments, the target nucleic acid polymer subunit of a kind is selectively modified or a modified subunit analog is substituted in a new analyte sequence, and the modified subunit is subsequently converted to an abasic site with an error correction enzyme.

In some embodiments, step (c) comprises:

(i) comparing the measured ion current to an ion current corresponding to a reference polymer comprising the subunit without the modification; and (ii) detecting the presence or absence of a difference in the ion currents compared in step (i), wherein the presence or absence of a difference in ion currents indicates the presence or absence of the subunit modification in the polymer analyte, respectively.

In some embodiments, the reference polymer comprises or consists of the same sequence as the pre-analyte polymer.

In some embodiments, the method further comprises translocating the reference polymer from the first conductive liquid medium to the second conductive liquid medium through the nanopore and measuring an ion current to provide the ion current corresponding to the reference polymer. In some embodiments, the method further comprises determining the position of the modified subunit in the polymer analyte based on a characteristic of the measured ion current. In some embodiments, the method further comprises determining the identity of the target polymer subunit at a position in the pre-analyte polymer sequence that corresponds to the position of the modified subunit in the polymer analyte.

In some embodiments, the method further comprises:

performing the step of selectively modifying a target polymer subunit and steps (a) and (b) for a plurality pre-analyte polymers that comprise a common sequence;

producing a consensus map of the plurality of ion currents measured in step (b); and detecting the presence of multiple modified subunits in the common sequence.

In some embodiments, the method further comprises:

performing the step of selectively modifying a target polymer subunit and steps (a) and (b) for a plurality pre-analyte polymers that comprise a common sequence;

producing a consensus map of the plurality of ion currents measured in step (b);

comparing the consensus map to the ion current corresponding to the reference polymer comprising the subunit without the modification; and detecting the presence of multiple differences between the consensus map and the ion current corresponding to a reference polymer, wherein the presence or absence of multiple differences indicate the presence of multiple modified subunits in the common sequence.

In another aspect, the present disclosure provides a method for analyzing a nucleic acid analyte. The method comprises:

(a) incorporating a modified nucleobase into the nucleic acid analyte;

(b) contacting the nucleic acid analyte with an error correction enzyme capable of removing the modified nucleobase to provide an abasic site in the nucleic acid analyte;

(c) translocating the nucleic acid analyte from a first conductive liquid medium to a second conductive liquid medium through a nanopore, wherein the nanopore provides liquid communication between the first conductive liquid medium and the second conductive liquid medium;

(d) measuring an ion current between the first conductive liquid medium and the second conductive liquid medium as the nucleic acid analyte passes through the nanopore; and (e) detecting the abasic site based on the measured ion current.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
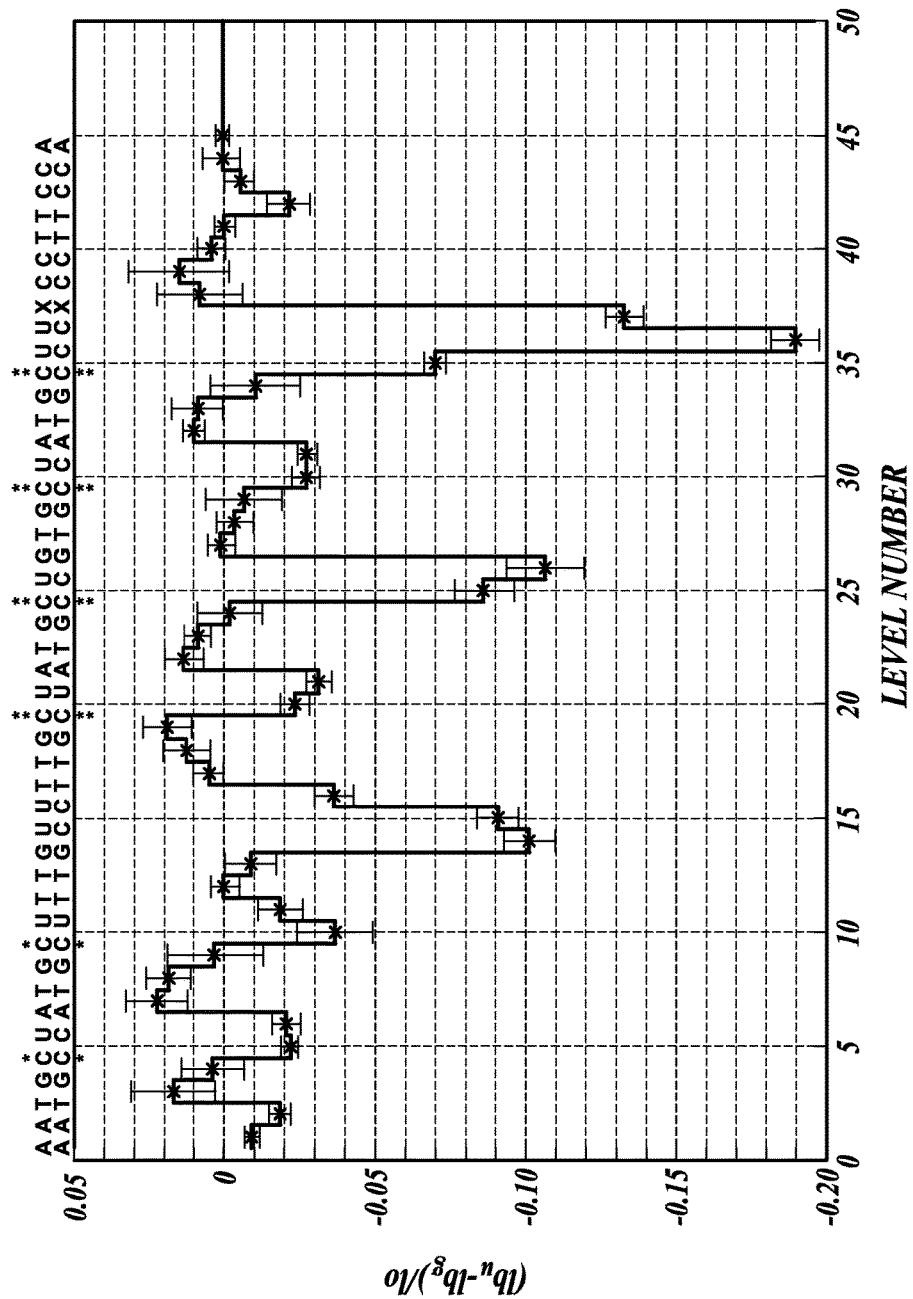
FIG. 1 illustrates the current differences obtained in a nanopore system by substituting cytosine residues (lower sequence, set forth in SEQ ID NO:9 and illustrated here in 3' to 5' orientation) for uracil residues (upper sequence, set forth in SEQ ID NO:8 and illustrated here in 3' to 5' orientation), but preserving the 5-hydroxymethyl cytosine (*) and 5-methyl cytosine (**)

The present disclosure generally relates to compositions and methods to efficiently analyze polymer characteristics. In some aspects, the present disclosure provides methods and compositions to generate and/or analyze modifications specific implemented to a target polymer subunit type. Such modifications can emphasize, or result in, differences in the detectable signals produced by a nanopore system. The differences enhance the ability to distinguish the various subunits present in the polymer.

Nanopores hold promise for inexpensive, fast, and nearly "reagent-free" analysis of polymers. In a general embodiment of a nanopore system, an external voltage is applied across a nanometer-scale, electrolyte-filled pore, inducing an electric field. Any analyte, such as a polymer that contacts, resides in, or moves through, the interior of the pore, modulates the ionic current that passes through the pore depending on its physical characteristics. If the interior tunnel formed by the pore is of sufficiently small diameter and length, polymers that pass through must pass in a linear fashion, such that only a subset of the polymer subunits reside in the most constricted zone of the pore tunnel at one time. Thus, the ionic current fluctuates over time as the polymer passes through the nanopore, subunit by subunit, depending on the different physical characteristics of the subunit(s) residing in the nanopore constriction zone at each iterative step. The fluctuation of the measured ionic current can be correlated to the subunits as they pass through, thus providing information regarding the sequence of subunit types in the polymer (i.e., the sequential order of identifiable subunit types).

As described above, a major challenge for nanopore-based analysis of polymers is establishing a nanopore system wherein each specific subunit type in the polymer results in a distinguishable and characteristic signal. Improvements to nanopores and nanopore systems have been designed to slow the translocation of polymer analytes through the nanopores and to result in more distinguishable signals for each monomeric subunit. However, the present inventors have developed an alternative approach that can be readily applied to all nanopore systems. As described in more detail below, the inventors have discovered that selective modifications to specific subunits of polymer to be analyzed can be implemented that result in signal differences from what would have been observed for the original, unmodified subunits. As a result, the presence of the specific monomeric subunits in the polymer can be discriminated by predictable changes in detectable signals caused by the modifications to those monomeric subunits, if present. Accordingly, when such a change in signal is detected, a practitioner can readily infer the presence of the specific monomeric subunit while reducing the potential confusion with signals representing other monomeric subunit types. This information can be applied to determine the overall sequence of the polymer analyte. In some embodiments, the modifications result in a signal change that is readily distinguishable from signals corresponding to any other monomeric subunit type, and thus the mere presence of the new signal is sufficient to establish the presence (and location) of the modified subunit and the original, unmodified subunit, in the polymer sequence.

In accordance with the foregoing, in one aspect, the present disclosure provides a method for analyzing a polymer analyte. The method comprises translocating a polymer analyte comprising a modified subunit from a first conductive liquid medium to a second conductive liquid medium through a nanopore, wherein the nanopore provides liquid communication between the first conductive liquid medium and the second conductive liquid medium. The method further comprises measuring an ion current between the first conductive liquid medium and the second conductive liquid medium as the polymer analyte passes through the nanopore. The method further comprises detecting the modified subunit based on the measured ion current.

The disclosed generally addresses methods to facilitate the analysis of any polymer analyte amenable to analysis in a nanopore-based system. As used herein, the term "polymer" refers to a chemical compound comprising two or more repeating structural units, generally referred to herein interchangeably as "subunits," "monomeric units," or "mers," where each subunit can be the same or different. Depending on the type of polymer, the potential subunits at each position can be selected from a group of identifiable subunit structures. Nonlimiting examples of polymers to be analyzed with the present methods include: nucleic acids, polypeptides, and proteins, as well as a variety of hydrocarbon polymers (e.g., polyethylene, polystyrene) and functionalized hydrocarbon polymers, wherein the backbone of the polymer comprises a carbon chain (e.g., polyvinyl chloride, polymethacrylates). Polymers can include copolymers, block copolymers, and branched polymers such as star polymers and dendrimers.

In some embodiments, the polymer is or comprises a nucleic acid. The term "nucleic acid" refers to a deoxyribonucleotide polymer (DNA) or ribonucleotide polymer (RNA) in either single- or double-stranded form. The structure of the canonical polymer subunits of DNA, for example, are commonly known and are referred to herein as adenine (A), guanine (G), cytosine (C), and thymine (T). As a group, these are generally referred to herein as nucleotides or nucleotide residues. For RNA, the canonical polymer subunits are the same, except with uracil (U) instead of thymine (T).

In some embodiments, the polymer is or comprises a polypeptide, i.e., the polymer is or comprises a sequence of multiple amino acid residues. As used herein, an "amino acid" refers to any of the 20 naturally occurring amino acids found in proteins, D-stereoisomers of the naturally occurring amino acids (e.g., D-threonine), and nonnatural amino acids. Each of these types of amino acids is not mutually exclusive. α-Amino acids comprise a carbon atom to which is bonded an amino group, a carboxyl group, a hydrogen atom, and a distinctive group referred to as a "side chain." The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine).

The following abbreviations are used for the 20 naturally occurring amino acids: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Any of the foregoing examples of polymers can also include noncanonical subunits or analogs. Noncanonical subunits can be useful to provide an obvious output signal to indicate that the end of a reference domain has passed through the nanopore. Regarding embodiments of nucleic acid polymers, illustrative and nonlimiting examples of noncanonical subunits include uracil (for DNA), 5-methylcytosine, 5-hydroxymethylcytosine, 5-formethylcytosine, 5-carboxycytosine b-glucosyl-5-hydroxy-methylcytosine, 8-oxoguanine, 2-amino-adenosine, 2-amino-deoxyadenosine, 2-thiothymidine, pyrrolo-pyrimidine, 2-thiocytidine, or an abasic lesion or site. An abasic site is a location along the deoxyribose backbone that is lacking a base. Known analogs of natural nucleotides hybridize to nucleic acids in a manner similar to naturally occurring nucleotides, such as peptide nucleic acids (PNAs) and phosphorothioate DNA.

Representative noncanonical peptide residues are known in the art, as set forth in, for example, Williams et al., *Mol. Cell. Biol.* 9:2574 (1989); Evans et al., *J. Amer. Chem. Soc.* 112:4011-4030 (1990); Pu et al., *J. Amer. Chem. Soc.* 56:1280-1283 (1991); Williams et al., *J. Amer. Chem. Soc.* 113:9276-9286 (1991); and all references cited therein. Exemplary noncanonical amino acids include, but are not limited to: 2-Aminoadipic acid, N-Ethylasparagine, 3-Aminoadipic acid, Hydroxylysin, β-alanine, β-Aminopropionic acid, allo-Hydroxylysine, 2-Aminobutyric acid, 3-Hydroxyproline, 4-Aminobutyric acid, piperidinic acid, 4-Hydroxyproline, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, N-Ethylglycine. Methods of incorporating noncanonical amino acids are well known in the art.

In some embodiments, a single polymer can comprise a combination of any of the foregoing polymers and/or polymer subunits. For example, in some embodiments, the polymer analyte is a combination of any two or more of DNA, RNA, PNA, and or polypeptide.

As used herein, the term "polymer analyte" refers to a polymer that is subjected to analysis in a nanopore-based system, the nanopore system being described in more detail below. In some embodiments, the polymer analyte can be derived from, or reflect the sequence of, a pre-analyte polymer. As used herein, the term "pre-analyte polymer" refers to a polymer that with an original sequence of monomeric subunits. As described above, the pre-analyte polymer can be any one of DNA, RNA, PNA, polypeptide, or a combination thereof. In some embodiments, the pre-analyte polymer comprises a nucleic acid. In further embodiments, the nucleic acid is DNA or RNA. The sequence of the pre-analyte polymer does not need to be known a priori, but in some embodiments can be inferred through the analysis facilitated by the disclosed method. The polymer analyte comprises a subunit that is modified relative to the corresponding subunit in the pre-analyte polymer. In this context, the term "modified" indicates a structural change exists in the subunit of the polymer analyte that results in a distinguishable signal from the signal produced by the corresponding unmodified or original subunit in the pre-analyte polymer.

In some embodiments, the method further comprises selectively modifying the target polymer subunit of a kind in a pre-analyte polymer prior to the translocating step, thereby producing the polymer analyte comprising a modified subunit. As used herein, the phrase "selectively modifying the target polymer subunit of a kind" refers to modifying one or more iterations of a singly kind (i.e., type) of monomeric subunit. For example, in embodiments where the pre-analyte polymer is DNA, the target polymer subunit could be any one type or kind of subunit, i.e., any specific type of nucleobase (e.g., adenine (A), thymine (T), cytosine (C), or guanine (G)). In embodiments where the pre-analyte polymer is RNA, the target polymer subunit could be any one type or kind of subunit, i.e., any specific type of nucleobase (e.g., adenine (A), uracil (U), cytosine (C), or guanine (G)). As a specific illustrative example, the target subunit type can be cytosine (C), which is subject to selective modification, wherein none of the other types (A, T, or G in this DNA example) are modified. When starting with a pre-analyte polymer with an unknown sequence, it will not be known a priori if any C subunits exist, how many C subunits exist, or where any C subunits exist in the sequence. However this knowledge is not necessary.

Regardless of any a priori knowledge, or lack thereof, the specific number of target polymer subunits of a kind that are modified is limited only by the number of the polymer subunits of a kind in the pre-analyte polymer sequence. The present method encompasses the modification of less than all of the existing target polymer subunits of a kind even though a multitude of target polymer subunits of a kind exists in the pre-analyte polymer. In one embodiment, one of the existing target polymer subunits of a kind is modified. For example, even if the pre-analyte polymer comprises a multitude of target cytosine subunits in the sequence, only one of the cytosine subunits is modified. In another embodiment, more than one of the existing target polymer subunits of a kind are modified. In yet another embodiment, all of the existing target polymer subunits of a kind are modified. As described in more detail below, in embodiments where less than all of the target polymer subunits of a kind are modified, the analysis can be performed on multiple copies of the pre-analyte polymer to produce a plurality of measured ion currents. A consensus of the plurality of ion currents can then be used to locate all locations of the target polymer subunits of a kind within the original sequence of the pre-analyte sequence.

In some embodiments, the step of modifying the target polymer subunit of a kind comprises contacting the pre-analyte polymer with an agent, wherein the agent is capable of selectively modifying the target polymer subunit of a kind in the pre-analyte polymer. As described above, the modification is selective in that polymer subunits of any other kind are not modified by the agent.

In one embodiment, the pre-analyte polymer is or comprises a nucleic acid. In a further embodiment, the kind of target polymer subunit is selected from adenine (A), thymine (T), cytosine (C), guanine (G), or uracil (U) (in RNA).

In one embodiment, the kind of target polymer subunit is cytosine. In a further embodiment, a target cytosine polymer subunit is selectively modified by converting the cytosine nucleobase to a uracil nucleobase. This conversion is also referred to as deamination of a cytosine nucleobase. Deamination of cytosine can be performed by any of a variety of known agents. As non-limiting examples, selective deamination of cytosine into uracil can be performed by agents including bisulfite, cytosine deaminase, NO, $N_2O_3$, and echinomycin, and the like. See, e.g., Caulfield, J. L., et al., "Nitric Oxide-induced Deamination of Cytosine and Guanine in Deoxynucleosides and Oligonucleotides," *The Journal of Biological Chemistry*, 273:12689-12695 (1998) and Moyer, R., et al., "Echinomycin, a bis-intercalating agent, induces C→T mutations via cytosine deamination," *Mutation Research/Fundamental and Molecular Mechanisms of Mutagenesis* 228:291-300 (1993), each of which is incorporated herein by reference in its entirety.

In some embodiments, the resulting uracil is further converted into an abasic site in the polymer. As described above, an abasic site is a location along the deoxyribose backbone that is lacking a base (e.g., lacking a nucleobase subunit). However, in contrast to a deletion mutation, in an abasic site, the site itself remains and is not excised from the polymer. As described in more detail below, abasic sites in nucleic acid polymers cause very distinctive signals in nanopore systems, which tend not to overlap with any signal resulting from any other possible subunit type. Accordingly, upon conversion of a uracil into an abasic site, the resulting polymer can be used as the analyte polymer in translocation step of the method.

In other embodiments, the conversion of the uracil into an abasic site comprises contacting the pre-analyte polymer with a nucleic acid error correction enzyme. Error correction enzymes for nucleic acids are well-known and can be used to locate and remove non-canonical nucleobases (e.g., modified nucleobase subunits) from nucleic acid polymers. For example, in one embodiment, the nucleic acid error correction enzyme is uracil deglycosylase (UNG) or an analog thereof. Other nucleic acid error correction enzymes that can convert uracil nucleobases to abasic sites are known and are encompassed by this method.

In one embodiment, the kind of target polymer subunit is cytosine and one or more cytosine subunits in the pre-analyte polymer are selectively modified by methylation. In one embodiment, the one or more cytosine subunits are methylated directly by contacting the pre-analyte polymer with a methyltransferase enzyme. Methyltransferases do not necessarily methylate every target subunit of a type (e.g., every cytosine in the sequence). However, multiple, identical pre-analyte polymers can be similarly treated and consensus signals can be compiled to ascertain the aggregate distribution of target subunits of the type. In another embodiment, the cytosine subunits can be methylated by substitution during the creation of a new pre-analyte polymer using, for example, either primer extension or PCR approaches. For example, the one or more cytosine subunits in the pre-analyte polymer can be selectively methylated by incorporating a methyl-cytosine analog into the pre-analyte polymer sequence in place of the cytosine residue using a polymerase enzyme. In this embodiment, the original dNTP mix provided would incorporate methyl-d triphosphate, such as for example 5-methyl-dCTP in place of dCTP. The resulting polymer in this example would have a sequence with 5-methylcytosines in place of cytosines.

In further embodiments, the step of selectively modifying the one or more cytosine residue(s) further comprises converting the methylated cytosine residue into an abasic site, thereby producing the polymer analyte. In some embodiments, converting the methylated cytosine residue into an abasic site comprises contacting the pre-analyte polymer with a nucleic acid error correction enzyme. As above, the error correction enzyme can be any enzyme capable of recognizing modifications to the canonical nucleic acid nucleobases and removing them to result in an abasic site. As a non-limiting example, DNA glycosylases are the main family of repair enzymes that can be used. DNA glycosylases fall into two categories: "pure" glycosylases and AP (apurinic/apyrimidinic) lyase/glycosylases. The pure glycosylases leave an abasic site in the DNA, whereas the AP lyase/glycosylases leave an AP site with a nick that would cause a single strand of DNA to break. 5-methylcytosine DNA glycosylase is an example of a nucleic acid (e.g., DNA) error correction enzyme that removes 5-methylcytosine bases from DNA polymers.

In one embodiment, the kind of target polymer subunit is guanine and one or more guanine subunits in the pre-analyte polymer are selectively modified by methylation. As above in the context of cytosines, in one embodiment, the one or more guanine subunits are methylated directly by contacting the pre-analyte polymer with a methyltransferase enzyme. Methyltransferases do not necessarily methylate every target subunit of a type (e.g., every guanine in the sequence). However, multiple copies of the pre-analyte polymers can be similarly treated and consensus signals can be compiled to ascertain the aggregate distribution of target subunits of the type. In another embodiment, the guanine subunits can be methylated by substitution during the creation of a new pre-analyte polymer using, for example, either primer extension or PCR approaches. In one further embodiment, the methylated guanine is a 3-methylguanine. In another embodiment, the methylated guanine is a 7-methylguanine. As described above, the methylated guanines can be implemented by substitution in the re-encoded pre-analyte polymer using PCR or primer extension reaction approaches. In such approaches, the provided dNTP mix can contain a 3-methyl-dGTP or 7-methyl-dGTP in place of dGTP.

In further embodiments, the step of selectively modifying the one or more guanine residue(s) further comprises converting the methylated guanine residue into an abasic site, thereby producing the polymer analyte. In some embodiments, converting the methylated cytosine residue into an abasic site comprises contacting the pre-analyte polymer with a nucleic acid (e.g., DNA) error correction enzyme, as described above. An illustrative, non-limiting example of a nucleic acid (e.g., DNA) DNA error correction enzymes is alkA (from *E. coli*) to remove the 7-methyl-guanine bases. See, e.g., Parikh, S. S., et al., "Base excision repair enzyme family portrait: integrating the structure and chemistry of an entire DNA repair pathway," *Structure* 5(12):1543-1550 (1997), incorporated herein by reference in its entirety. Illustrative, non-limiting examples of nucleic acid (e.g., DNA) DNA error correction enzymes to remove 3-methyl-guanine include alkA (from *E. coli*), tag (also referred to as "3-methyladenine DNA glycosylase I", from *E. coli*), MAG (from *S. cerevisiae*), MPG (from *M. musculus* or *H. sapiens*). See, e.g., Bjelland, S., et al., "Excision of 3-methyl-guanine from alkylated DNA by 3-methyladenine DNA glycosylase I of *Escherichia coli*," *Nucleic Acids Res.* 21(9):2045-2049 (1993); Bjørås, M., et al., "Purification and properties of the alkylation repair DNA glycosylase encoded the MAG gene from *Saccharomyces cerevisiae*," *Biochemistry* 34(14):4577-4582 (1995); and Roy, R., et al., "Distinct substrate preference of human and mouse N-methylpurine-DNA glycosylases," *Carcinogenesis* 17(10):2177-2182 (1996), each reference is incorporated herein by reference in its entirety.

It will be readily appreciated by persons of skill in the art that selective modifications to target nucleic acid subunits of a type (any of A, T, G, C, or U), other than methylation events, can also be applied to pre-analyte nucleic acid polymers. Thus, for example, target nucleobase subunits can be subject to other modifications according to similar approaches (e.g., directly with the appropriate selective agents, or by substitution in PCR or primer extension reactions to re-encode the pre-analyte polymer sequence). The resulting modified subunits can be converted to abasic sites using the appropriate nucleic acid (e.g., DNA) error correction enzymes. For example, adenine subunits can be specifically targeted for deamination to provide hypoxanthine subunits. These subunits can be detected and removed by the DNA error correction enzyme alkA from *E. coli* (Magi in yeast, MPG in human). As another example, the DNA error correction enzyme, Fpg (formamidopyrimidine [fapy]-DNA glycosylase) (also known as 8-oxoguanine DNA glycosylase), recognizes such 7,8-dihydro-8-oxoguanine (8-oxoguanine) and 8-oxoadenine, which are non-methylated base alterations. While this enzyme also contains lyase activity, which can result in cleaving the DNA after creating the abasic site, the lyase activity can be readily inhibited through standard approaches, such as molecular engineering of the active site for lyase activity.

In many embodiments, the modification of one or more target subunits of a type in the pre-analyte polymer to produce an analyte polymer comprising a modified subunit will be sufficient to result in a detectable ion current that distinctly signals the presence of the modification. For example, the conversion of any nucleic acid subunit to an abasic site is generally expected to produce a distinct signal in most nanopore systems that does not overlap with any ion current signal from the remaining nucleic acid subunits. However, in some embodiments, the presence of a modified subunit produces a different ion current, but one that may now overlap with the ion current produced by another existing subunit of a different type. Accordingly, it is the presence of a change in the ion current signal that indicates the presence of a modified subunit at a particular location in the sequence. Thus, in some embodiments of the method, the step of detecting a modified subunit comprises: comparing the measured ion current to an ion current corresponding to a reference polymer comprising the subunit without the modification; and detecting the presence or absence of a difference in the compared ion currents, wherein the presence or absence of a difference in ion currents indicates the presence or absence of the subunit modification in the polymer analyte, respectively.

In some embodiments, the reference polymer comprises the same sequence as the pre-analyte polymer. In some embodiments, the reference polymer consists of the same sequence as the pre-analyte polymer. Thus, in some embodiments, the reference polymer is the pre-analyte polymer.

In some embodiments, the method further comprises translocating the reference polymer from the first conductive liquid medium to the second conductive liquid medium through the nanopore and measuring an ion current to provide the ion current corresponding to the reference polymer. In some embodiments, the method further comprises determining the position of the modified subunit in the polymer analyte based on a characteristic of the measured ion current for the polymer analyte. In some embodiments, the characteristic of the measured ion current is a difference, or range of difference, between the ion current for the polymer analyte and the ion current for the reference polymer. In some embodiments, the method comprises determining the identity of the target polymer subunit at a position in the pre-analyte polymer sequence that corresponds to the position of the modified subunit in the polymer analyte.

It will be appreciated that for cases of DNA analytes, where a positive (or sense) strand complements with a negative (or antisense) strand, the analysis can be performed on a first strand to ascertain the position or positions of a first target polymer subunit of a kind in the first strand. The same analysis can be performed on the complement strand (e.g., the second strand), which will indicate the position or positions of a second target polymer subunit of a kind in the first strand due to the complementarity of the first and second strands. For example, a sense strand of DNA can be subjected to modifications wherein the cytosines are converted to uracils (and possibly modified further into abasic sites), as described herein, to result in a first polymer analyte. The modified subunits will produce distinguishable ion current signals that indicate the positions of the original cytosines in the original pre-analyte sense strand of DNA. The same modification can be performed on the antisense strand of DNA, which is a complement of the first strand, to produce a second polymer analyte. The ion current signals resulting from the second polymer analyte indicate the positions of the original cytosines in the original pre-analyte antisense strand. Because the cytosine residues in the original pre-analyte antisense strand complement with guanine residues in the original pre-analyte sense strand, this analysis of the second polymer analyte (the antisense strand) provides the locations of the guanines in the original pre-analyte sense strand. Thus, two of the four types of polymer subunits for the sense strand are clearly identified. In the context of MspA nanopore systems, the adenine and thymine residues produce readily distinguishable ion currents, whereas cytosine and guanine residues often have overlapping ion currents. By successfully identifying the positions of both the cytosine and guanine residues, the entire sequence can be ascertained with a high level of certainty.

As described above, in some instances less than all of the existing target polymer subunits of a type are modified. This may be due to a limitation of the agents used, or the inability of the polymer to stably incorporate all of the changes. Thus, in some embodiments of the method, the steps of selectively modifying a target polymer subunit to provide a polymer analyte, translocating the polymer analyte, and measuring an ion current, are performed for a plurality pre-analyte polymers that comprise a common sequence. In this embodiment, a consensus map of the plurality of measured ion currents is generated and the presence of modified subunits is detecting in the common sequence. In further embodiments where the presence of modified subunits is determined by a different in ion current signal from a reference signal, the steps of selectively modifying a target polymer subunit to provide a polymer analyte, translocating the polymer analyte, and measuring an ion current, are performed for a plurality pre-analyte polymers that comprise a common sequence; producing a consensus map of the plurality of measured ion currents; comparing the consensus map to the ion current corresponding to the reference polymer comprising the subunit without the modification; and detecting the presence of multiple differences between the consensus map and the ion current corresponding to a reference polymer, wherein the presence or absence of multiple differences indicate the presence of multiple modified subunits in the common sequence.

In another aspect, the disclosure provides a method for analyzing a nucleic acid analyte, comprising:

(a) incorporating a modified nucleobase into the nucleic acid analyte;

(b) contacting the nucleic acid analyte with an error correction enzyme capable of removing the modified nucleobase to provide an abasic site in the nucleic acid analyte;

(c) translocating the nucleic acid analyte from a first conductive liquid medium to a second conductive liquid medium through a nanopore, wherein the nanopore provides liquid communication between the first conductive liquid medium and the second conductive liquid medium;

(d) measuring an ion current between the first conductive liquid medium and the second conductive liquid medium as the nucleic acid analyte passes through the nanopore; and (e) detecting the abasic site based on the measured ion current.

As described above, the modified nucleobase can be created directly using known agents that selectively create a structural change in a target nucleobase, such as methylation, deamination, oxidation, and the like. Alternatively, the nucleic acid analyte can be re-encoded with the target nucleobase substituted with the modified nucleobase of choice using the appropriate modification to the dNTP mix (as described above and illustrated below). Subsequently, the nucleic acid analyte is contacted with an error correction enzyme, such as a DNA correction enzyme, which are well-known in the art and are generally described above. It will be apparent to persons skilled in the art that this strategy can address any of nucleic acid subunit type, such as adenine (A), guanine (G), cytosine (C), and thymine (T) (or uracil (U) in RNA).

Various aspects of the nanopore and nanopore system will now be described. A "nanopore" specifically refers to a pore having an opening with a diameter at its most narrow point of about 0.3 nm to about 2 nm. Nanopores useful in the present disclosure include any pore capable of permitting the linear translocation of a polymer from one side to the other at a velocity amenable to monitoring techniques, such as techniques to detect current fluctuations. In some embodiments, the nanopore comprises a protein, such as alpha-hemolysin, *Mycobacterium smegmatis* porin A (MspA), OmpATb, homologs thereof, or other porins, as described in U.S. Pub. No. US2012/0055792, International PCT Pub. Nos. WO2011/106459, WO2011/106456, and Manrao et al., "Reading DNA at single-nucleotide resolution with a mutant MspA nanopore and phi29 DNA polymerase," *Nat. Biotechnol.* 30:349-353 (2012), each of which is incorporated herein by reference in its entirety. A "homolog," as used herein, is a gene from another bacterial species that has a similar structure and evolutionary origin. By way of an example, homologs of wild-type MspA, such as MppA, PorM1, PorM2, and Mmcs4296, can serve as the nanopore in the present invention. Protein nanopores have the advantage that, as biomolecules, they self-assemble and are essentially identical to one another. In addition, it is possible to genetically engineer protein nanopores to confer desired attributes, such as substituting amino acid residues for amino acids with different charges, or to create a fusion protein (e.g., an exonuclease+alpha-hemolysin). Thus, the protein nanopores can be wild-type or can be modified to contain at least one amino acid substitution, deletion, or addition. In some embodiments the at least one amino acid substitution, deletion, or addition results in a different net charge of the nanopore. In some embodiments, the different in net charge increases the difference of net charge as compared to the first charged moiety of the polymer analyte. For example, if the first charged moiety has a net negative charge, the at least one amino acid substitution, deletion, or addition results in a nanopore that is less negatively charged. In some cases, the resulting net charge is negative (but less so), is neutral (where it was previously negative), is positive (where is was previously negative or neutral), or is more positive (where it was previously positive but less so).

Descriptions of modifications to MspA nanopores have been described, see U.S. Pub. No. 2012/0055792, incorporated herein by reference in its entirety. Briefly described, MspA nanopores can be modified with amino acid substitutions to result in a MspA mutant with a mutation at position 93, a mutation at position 90, position 91, or both positions 90 and 91, and optionally one or more mutations at any of the following amino acid positions: 88, 105, 108, 118, 134, or 139, with reference to the wild type amino acid sequence. In one specific embodiment, the MspA contains the mutations D90N/D91N/D93N, with reference to the wild type sequence positions (referred to therein as "M1MspA" or "M1-NNN"). In another embodiment, the MspA contains the mutations D90N/D91N/D93N/D118R/D134R/E139K, with reference to the wild type sequence positions (referred to therein as "M2MspA"). See U.S. Pub. No. 2012/0055792. Such mutations can result in a MspA nanopore that comprises a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel. Furthermore, the amino acid substitutions described in these examples provide a greater net positive charge in the vestibule of the nanopore, further enhancing the energetic favorability of interacting with a negatively charged polymer analyte end.

In some embodiments, the nanopores can include or comprise DNA-based structures, such as generated by DNA origami techniques. For descriptions of DNA origami-based nanopores for analyte detection, see PCT Pub. No. WO2013/083983, incorporated herein by reference.

In some embodiments, the nanopore can be a solid state nanopore. Solid state nanopores can be produced as described in U.S. Pat. Nos. 7,258,838 and 7,504,058, incorporated herein by reference in their entireties. Solid state nanopores have the advantage that they are more robust and stable. Furthermore, solid state nanopores can in some cases be multiplexed and batch fabricated in an efficient and cost-effective manner. Finally, they might be combined with micro-electronic fabrication technology. In some embodiments, the nanopore comprises a hybrid protein/solid state nanopore in which a nanopore protein is incorporated into a solid state nanopore. In some embodiments, the nanopore is a biologically adapted solid-state pore.

In some embodiments, such as incorporating MspA protein nanopores, the nanopore comprises a vestibule and a constriction zone that together form a tunnel. A "vestibule" refers to the cone-shaped portion of the interior of the nanopore whose diameter generally decreases from one end to the other along a central axis, where the narrowest portion of the vestibule is connected to the constriction zone. A vestibule may generally be visualized as "goblet-shaped." Because the vestibule is goblet-shaped, the diameter changes along the path of a central axis, where the diameter is larger at one end than the opposite end. The diameter may range from about 2 nm to about 6 nm. Optionally, the diameter is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. The length of the central axis may range from about 2 nm to about 6 nm. Optionally, the length is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. When referring to "diameter" herein, one can determine a diameter by measuring center-to-center distances or atomic surface-to-surface distances.

A "constriction zone" refers to the narrowest portion of the tunnel of the nanopore, in terms of diameter, that is connected to the vestibule. The length of the constriction zone can range, for example, from about 0.3 nm to about 20 nm. Optionally, the length is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein. The diameter of the constriction zone can range from about 0.3 nm to about 2 nm. Optionally, the diameter is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein. In other embodiment, such as those incorporating solid state pores, the range of dimension (length or diameter) can extend up to about 20 nm. For example, the constriction zone of a solid state nanopore is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, or 20 nm, or any range derivable therein. Larger dimension in such nanopores can be preferable depending on the In some cases, the nanopore is disposed within a membrane, thin film, or lipid bilayer, which can separate the first and second conductive liquid media, which provides a nonconductive barrier between the first conductive liquid medium and the second conductive liquid medium. The nanopore, thus, provides liquid communication between the first and second conductive liquid media. In some embodiments, the pore provides the only liquid communication between the first and second conductive liquid media. The liquid media typically comprises electrolytes or ions that can flow from the first conductive liquid medium to the second conductive liquid medium through the interior of the nanopore. Liquids employable in methods described herein are well-known in the art. Descriptions and examples of such media, including conductive liquid media, are provided in U.S. Pat. No. 7,189,503, for example, which is incorporated herein by reference in its entirety. The first and second liquid media may be the same or different, and either one or both may comprise one or more of a salt, a detergent, or a buffer. Indeed, any liquid media described herein may comprise one or more of a salt, a detergent, or a buffer. Additionally, any liquid medium described herein may comprise a viscosity-altering substance or a velocity-altering substance.

The polymer analyte serving as the target or focus of an analysis is capable of interacting with the nanopore and translocating, preferably in a linear fashion, through the pore to the other side. As used herein, the terms "interact" or "interacting," indicate that the analyte moves into at least an interior portion of the nanopore and, optionally, moves through the nanopore. As used herein, the terms "through the nanopore" or "translocate" are used to convey for at least some portion (i.e., at least one subunit) of the polymer analyte to enter one side of the nanopore and move to and out of the other side of the nanopore. In some cases, the first and second conductive liquid media located on either side of the nanopore are referred to as being on the cis and trans regions, where the polymer analyte to be measured generally translocates from the cis region to the trans region through the nanopore. However, in some embodiments, the polymer analyte to be measured can translocate from the trans region to the cis region through the nanopore. In some cases, the entire length of the polymer does not pass through the pore, but portions or segments of the polymer pass through the nanopore for analysis.

The polymer analyte can be translocated through the nanopore using a variety of mechanisms. For example, the polymer analyte and/or reference sequence can be electrophoretically translocated through the nanopore. Nanopore systems also incorporate structural elements to apply an electrical field across the nanopore-bearing membrane or film. For example, the system can include a pair of drive electrodes that drive current through the nanopores. Additionally, the system can include one or more measurement electrodes that measure the current through the nanopore. These can be, for example, a patch-clamp amplifier or a data acquisition device. For example, nanopore systems can include an Axopatch-1B patch-clamp amplifier (Axon Instruments, Union City, Calif.) to apply voltage across the bilayer and measure the ionic current flowing through the nanopore. The electrical field is sufficient to translocate a polymer analyte through the nanopore. As will be understood, the voltage range that can be used can depend on the type of nanopore system being used. For example, in some embodiments, the applied electrical field is between about 20 mV and about 260 mV, for protein-based nanopores embedded in lipid membranes. In some embodiments, the applied electrical field is between about 40 mV and about 200 mV. In some embodiments, the applied electrical field is between about 100 mV and about 200 mV. In some embodiments, the applied electrical field is about 180 mV. In other embodiments where solid state nanopores are used, the applied electrical field can be in a similar range as described, up to as high as 1 V.

Additionally or alternatively, nanopore systems can include a component that translocates a polymer through the nanopore enzymatically. For example, a molecular motor can be included to influence the translocation of polymers through the nanopore. A molecular motor can be useful for facilitating entry of a polymer into the nanopore and/or facilitating or modulating translocation of the polymer through the nanopore. Ideally, the translocation velocity, or an average translocation velocity, is less than the translocation velocity that would occur without the molecular motor. In any embodiment herein, the molecular motor can be an enzyme, such as a polymerase, an exonuclease, or a Klenow fragment. In one example, described in more detail below, a DNA polymerase such as phi29 can be used to facilitate movement in both directions. See Cherf, G. M., et al., "Automated forward and reverse ratcheting of DNA in a nanopore at 5-A precision," Nat. Biotechnol. 30:344-348 (2012), and Manrao et al., "Reading DNA at single-nucleotide resolution with a mutant MspA nanopore and phi29 DNA polymerase," Nat. Biotechnol. 30:349-353 (2012), both of which are incorporated herein by reference in their entireties.

Characteristics of a polymer analyte such as identifying characteristics of some or all subunits thereof, can be determined in a nanopore system based on measurable effects of the residency of the polymer analyte in the nanopore. It will be readily understood that such determined characteristic of the polymer analyte can then be used to infer characteristics of the pre-analyte polymer. In some embodiments, information is determined about the one or more polymer subunits in the polymer analyte. Thus, as described above, the ion current resulting from a selectively modified analyte can be used to infer the original subunit at that position in the pre-analyte polymer. In some embodiments, the presence of one or more modified subunits can be used to infer the presence and pattern of a plurality of unmodified subunits in the pre-analyte polymer to provide a "fingerprint" or primary subunit sequence. In some embodiments, the sequence identity is determined for one, two, or more polymer subunits in the pre-analyte polymer. In some embodiments, the sequence of some or all of the pre-analyte polymer is determined.

Characteristics of polymer analyte, or of subunit(s) thereof, can be determined based on the effect of the polymer analyte, or subunit(s) thereof, on a measurable signal when interacting with the nanopore, such as interactions with the outer rim, vestibule, or constriction zone of the nanopore. To illustrate, in some embodiments, the polymer subunit(s) that determine(s) or influence(s) a measurable signal is/are the subunit(s) residing in the "constriction zone," i.e., the three-dimensional region in the interior of the pore with the narrowest diameter. Depending on the length of the constriction zone, the number of polymer subunits that influence the passage of electrolytes and, thus, the current output signal, can vary. The output signal produced by the nanopore system is any measurable signal that provides a multitude of distinct and reproducible signals depending on the physical characteristics of the polymer or polymer subunit(s). For example, the ionic current level through the pore is an output signal that can vary depending on the particular polymer subunit(s) residing in the constriction zone of the nanopore. As the polymer translocates in iterative steps (e.g., linearly, subunit by subunit through the pore), the current levels can vary to create a trace, or "current pattern," of multiple output signals corresponding to the contiguous sequence of the polymer subunits. This detection of current levels, or "blockade" events have been used to characterize a host of information about the structure polymers, such as DNA, passing through, or held in, a nanopore in various contexts.

In general, a "blockade" is evidenced by a change in ion current that is clearly distinguishable from noise fluctuations and is usually associated with the presence of an analyte molecule, e.g., one or more polymer subunits, within the nanopore such as in the constriction zone. The strength of the blockade, or change in current, will depend on a characteristic of the polymer subunit(s) present. Accordingly, in some embodiments, a "blockade" is defined against a reference current level. In some embodiments, the reference current level corresponds to the current level when the nanopore is unblocked (i.e., has no analyte structures present in, or interacting with, the nanopore). In some embodiments, the reference current level corresponds to the current level when the nanopore has a known analyte (e.g., a known analyte polymer subunit) residing in the nanopore. In some embodiments, the current level returns spontaneously to the reference level (if the nanopore reverts to an empty state, or becomes occupied again by the known analyte). In other embodiments, the current level proceeds to a level that reflects the next iterative translocation event of the polymer analyte through the nanopore, and the particular subunit(s) residing in the nanopore change(s). To illustrate, with respect to the reference current level defined as an unblocked level, the blockade is established when the current is lower than the reference current level by an amount of about 1-100% of the reference current level. It will be understood that the reference current level can immediately precede the blockade event or, alternatively, be separated from the blockade event by a period of time with intervening current measurements. For example, the ionic current may be lower than the reference current level by a threshold amount of about, at least about, or at most about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%, or any range derivable therein, of the reference current level when a polymer analyte subunit enters the nanopore. With respect to the reference current level defined by the presence of a known analyte (e.g., known polymer subunit(s)), the blockade is established when the current is lower or higher than the reference level by an amount of about 1 100% of the reference current level. It will be understood that the reference current level can immediately precede the blockade event or, alternatively, be separated from the blockade event by a period of time with intervening current measurements. For example, the ionic current may be lower or higher than the reference current level by threshold of about, at least about, or at most about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%, or any range derivable therein, of the reference current level when a polymer analyte subunit enters the nanopore. "Deep blockades" can be identified as intervals where the ionic current is lower (or higher) by at least 50% of the reference level. Intervals where the current drops by less than 50% of the reference level can identified as "partial blockades." In some embodiments, the current level in a blockade remains at the reduced (or elevated) level for at least about 1.0 µs.

In some embodiments, the measurable signal obtained from nanopore analysis of the polymer analyte is compared against a known signal or a signal obtained from a known analyte. The term "known analyte" is used in reference to an analyte for which the status with respect to a particular characteristic, such as subunit sequence, is known. In some embodiments, the known signal is obtained from the known analyte under the same or similar analytical conditions. In some embodiments, the comparison of measurable signals, such as current patterns obtained from an unknown polymer analyte and a reference standard polymer analyte permits the identification of an identifiable "fingerprint" that distinguishes the polymer analyte from other potential analytes. In some embodiments, the comparison of measurable signals, such as current patterns obtained from an unknown polymer analyte and a reference standard polymer analyte permits the identification of one or more polymer subunits in the analyte domain. It will be understood that in these embodiments, the current levels of corresponding polymer subunit identities in the unknown and reference polymer analyte do not have to match. Instead, the identities can be determined by their relative current levels among current levels corresponding to a finite selection of subunit identities.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

The following is a description of a comparison of ion currents determined for ssDNA polynucleotide molecules where the cytosine residues have been converted to uracil residues. This data demonstrates that such a modification in a polymer analyte can be used to provide signal changes to differentiate the cytosine residues, as well as the guanine residues in a complementary strand. Because the analysis can be performed on both strands, the locations of the cytosine and guanine residues can readily be identified for either strand.

The experimental setup was as previously described in Manrao et al., *Nature Biotechnol.* 30(4):349-353 (2012), which is incorporated by reference herein. Briefly, phi 29 DNAP was used as a molecular motor to control the motion of DNA through a single MspA pore established in an unsupported phospholipid bilayer. The buffer used as the conductive liquid media was 300 mM KCl with 10 mM HEPES, buffered at pH 8.00±0.05. Currents were recorded on an Axopatch 200B amplifier with custom LabVIEW software (National Instruments, Austin, Tex.) at a voltage bias of 180 mV.

Regular DNA oligonucleotides and DNA oligonucleotides containing uracil nucleobases in the place of cytosine nucleobases were purchased from the Protein and Nucleic Acid (PAN) facility at Stanford University. Primers and blocking oligomers that would conjugate to the strands were also ordered. See Table 1.

TABLE 1 oligonucleotides used to compare nanopore-based analyses of cytosine to uracil substitutions.

| Name | Sequence | SEQ ID NO: | Notes |
|---|---|---|---|
| mTGCC U Blocker | TTTTATTAGTTGCTT GATTTACGATACGAA ACGAAANNNNNNNZ | 2 | Z = a three carbon spacer |
| mTGCC U1 | PAAAAAAACCTTCCN UUZGTAUZGTGUZGT AUZGTTUUGTTUXGT AUXGTAAATCAAGCA ACTAATAAAAGCATT CTCATGCAGGTCGTA GCC | 3 | P = phosphorylated 5' end Z = methylated C X = hydroxy-methylated C |
| DNAP hp primer | GCGTACGCCTACGGT TTTCCGTAGGCGTAC GCGGCTACGACCTGC ATGAGAATGC | 4 | |
| Methyl TGCC | PAAAAAAACCTTCCN CCZGTACZGTGCZGT ACZGTTCCGTTCXGT ACXGTAAATCAAGCA ACTAATAAAAGCATT CTCATGCAGGTCGTA GCC | 5 | P = phosphorylated 5' end Z = methylated C X = hydroxy-methylated C |

Prior to each experiment, the DNA template, primer, and blocking oligomer were mixed together in a 1:1:1.2 ratio to a final concentration of 50 µM. DNA was then annealed by heating to 95° C. for five minutes, cooling to 60° C. for two minutes, and then cooling to 4° C. Experimental concentrations were ~500 nM for DNA, ~500 nM for phi 29 DNAP, ~500 µM for dNTPs, ~10 mM for $MgCl_2$~, and ~1 mM for DTT.

During strand sequencing, the DNA is passed through the pore twice, once in the 5' to 3' direction (unzipping mode) and once in the 3' to 5' direction (synthesis mode). In this report, data from the synthesis mode of phi29 DNAP motion were used. See Manrao et al., *Nature Biotechnol.* 30(4):349-353 (2012). All strands included an adapter sequence linked to the 5'end with the sequence 5'-PAAAAAAACCTTCCX-3', set forth herein as SEQ ID NO:1, where P represents a phosphorylated 5' end and X is an abasic residue. This sequence was not subject to modifications, as described below, and creates a reproducible current motif that signals the end of the read. This region was use to calibrate currents in order to control for small changes in buffer conductivity due to evaporation or temperature variation. The sequence of interest followed this calibration sequence.

FIG. 1 illustrates the ion current differences produced by polymer analytes passing through the MspA nanopore, where cytosine residues were replaced with uracil residues. The ion currents were specifically generated by passing the oligonucleotides "Methyl TGCC" (see SEQ ID NO:5) and "mTGCC U1" (see SEQ ID NO:3) through the MspA nanopore. mTGCC U1 is identical to Methyl TGCC except that the cytosines were replaced with uracils, while 5-methylcytosine ("5mC") and 5-hydroxymethylcytosine ("5hmC") remain consistent between the two oligonucleotides. The DNA oligonucleotides were ordered to mimic the effect of bisulfite treatment on DNA, where bisulfite treatment results in the conversion of cytosine to uracil. FIG. 1 illustrates the alignment of internal fragments of the "Methyl TGCC" DNA (bottom sequence, SEQ ID NO:9) and "mTGCC U1" DNA (top sequence, SEQ ID NO:8) sequences, as they align to the graphed differences in measured ionic current (the sequences are illustrated in the 3' to 5' orientation. Comparison of reads of untreated DNA with those of treated DNA yields the location of cytosine residues within the strand greatly simplifying the task of sequencing with nanopores. It is specifically noted that instances of two contiguous uracil residues results in a larger deviation than a single uracil residue. Additionally, a uracil followed by a guanine resulted in a larger current deviation, which can be distinguished from a double uracil by addressing the antisense strand (considering that the guanine would correspond to a cytosine in the antisense strand, and thus be amenable to conversion with this method). Furthermore, because cytosine residues pair with guanine residues in double stranded DNA molecules, the above analysis can be generally performed with both the sense and antisense strands of a double-stranded DNA molecule to yield the locations of every C and G along a single strand. The remaining steps to sequence the single strand molecule are greatly simplified, and address differentiating between A and T for the remaining unknown nucleotides. For MspA, the A and T residues are readily distinguishable because A causes the highest currents, while T causes the lowest currents.

Accordingly, it is shown that the conversion of cytosine residues to uracil residues in a DNA polymer analyte can be employed in a nanopore-based sequencing to differentiate the C residues in the sequence. Because the analysis can be performed on the sense and antisense strand of a double-stranded DNA molecule, the locations of both the C and G residues can be definitively defined.

The following is a description of a bisulfite treatment of a ssDNA pre-analyte polymer to produce a polymer analyte wherein the cytosine residues have been modified, or converted, to uracil residues. The subsequent nanopore analysis of both the modified polymer analyte and the initial pre-analyte polymer (as a reference) confirms the strategy that such chemical modification can facilitate the definitive discrimination of cytosine residues in the pre-analyte polymer sequence.

Bisulfite Treatment to Improve Nanopore Sequencing

Figure 3:
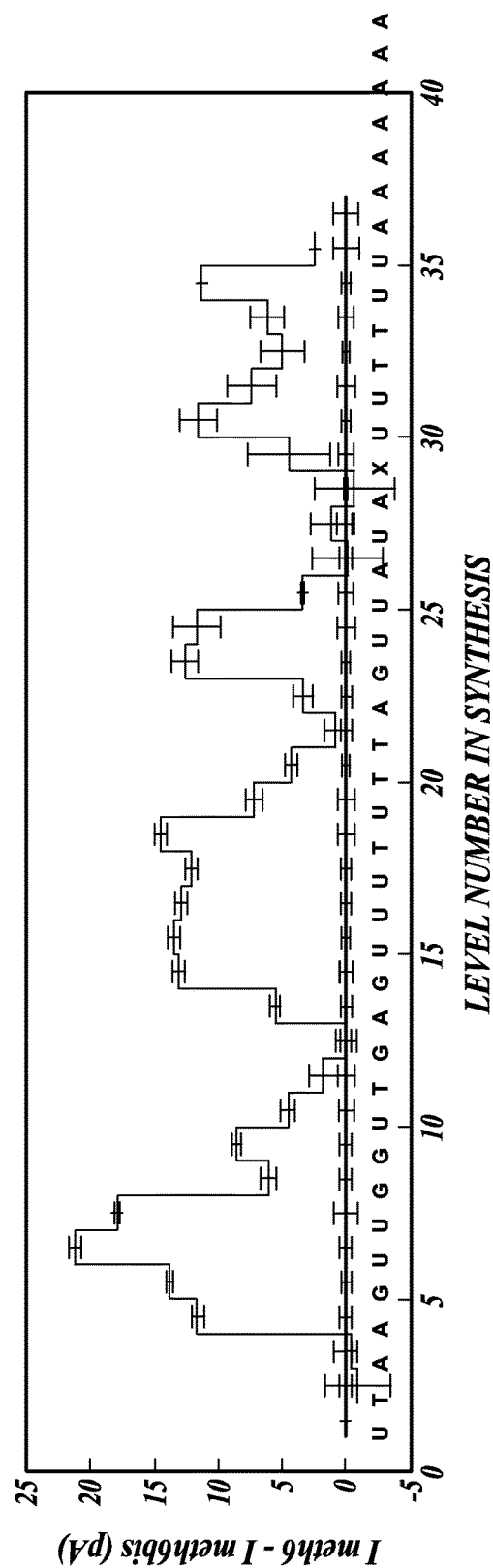
FIG. 3 illustrates the difference of current levels associated with the M6 DNA oligonucleotide compared to bM6 DNA oligonucleotide (M6 minus bM6). Most regions with C to U conversions have significantly diminished ion current. The ion currents are illustrated with reference to the analyte sequence, set forth as SEQ ID NO:7, illustrated here in the 3' to 5' orientation

A synthetic DNA construct with the sequence AAAAAAACCTTCCXACACCGATTCTCCCGAGTCG-GCCGAATC ("M6"), set forth herein as SEQ ID NO:6, was analyzed with the nanopore MspA+phi29 DNAP sequencing system (described above and in Manrao et al., *Nature Biotechnol.* 30(4):349-353 (2012)). This DNA construct was also subjected to a bisulfite conversion process (Zymo Research, Irvine, Calif.). The resulting DNA, comprising the sequence AAAAAAAUUTTUUXAUAUUGAT-TUTUUUGAGTUGGUUGAATU ("bM6"), set forth herein as SEQ ID NO:7 and illustrated in FIG. 3 in the 3' to 5' orientation, which had all cytosine residues converted to uracil residues, was also measured with the MspA nanopore sequencing system.

Results

Figure 2:
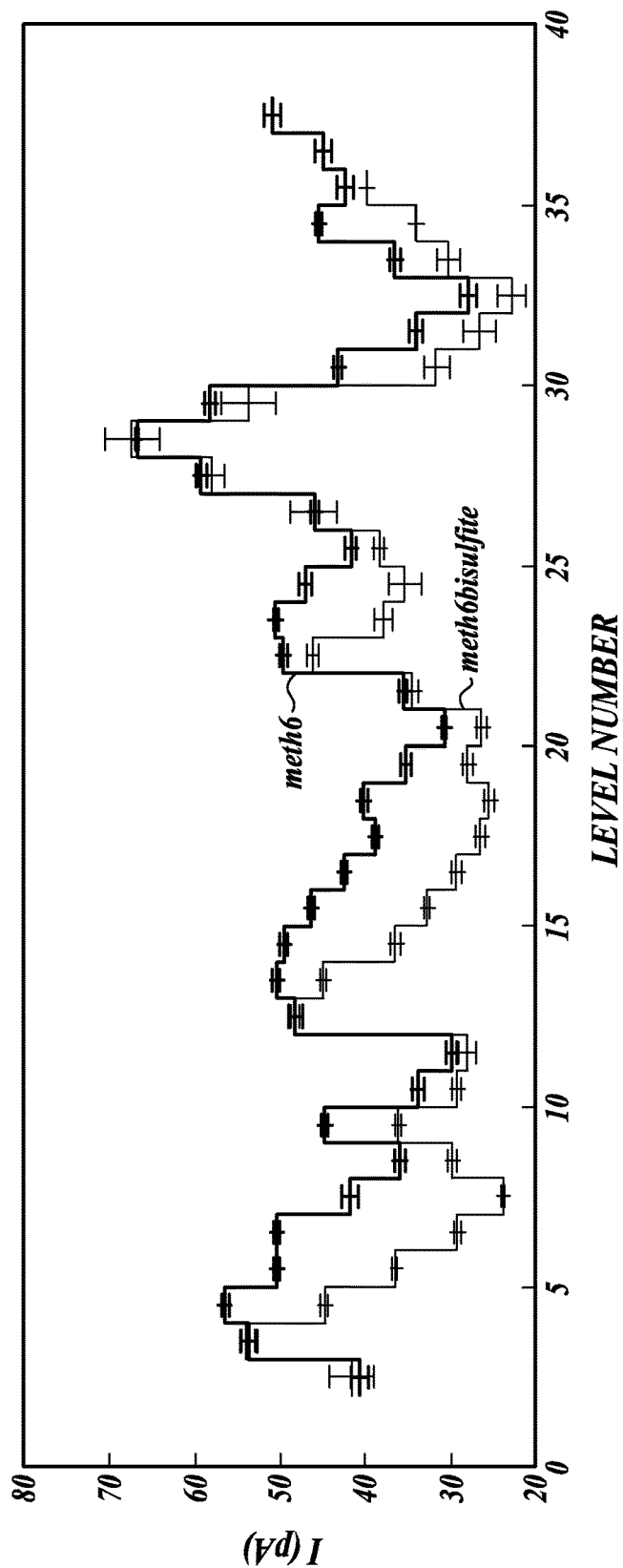
FIG. 2 illustrates the patterns of ionic current levels associated with the DNA oligonucleotides M6 ("meth6" dark line) and bM6 ("meth6bisulfite" light line)

The current level patterns associated with the sequences of the M6 and bM6 oligonucleotides, illustrated FIG. 2, were subject to data analysis tools similar to those used in Manrao et al., *Nature Biotechnol.* 30(4):349-353 (2012) and Laszlo, A. H., et al. "Detection and mapping of 5-methylcytosine and 5-hydroxymethylcytosine with nanopore MspA," *Proc. Natl. Acad. Sci. USA* 110: 18904-18909 (2013). The ion current level patterns were considerably different in a number of locations.

The bisulfite treated DNA oligonucleotides were observed to contain many levels that had consistently lower ion currents (see FIG. 2). Single cytosine to uracil conversion affects roughly four current levels near the site of the converted nucleotide. The effect of multiple adjacent cytosine to uracil conversions superimposes additively. It is expected that the context, i.e. the identity of nucleotides in the neighborhood of the cytosine to uracil conversion affect the magnitude of the signal. The uracil residues near to the abasic site (X) do not reveal significant ion current changes, likely because the abasic site mutes the impacts on the ion current of the nearby cytosine to uracil conversion. The ion current pattern near an abasic site is generally very different from ion currents several nucleotides away from X. These results are consistent with the findings from the preliminary comparative results described above. Furthermore, the uracil residue has a chemical structure that is similar to thymine, a base that has been associated with a significantly lower ion current (on the order of 20 pA). Taking the difference between the currents of the unmodified DNA and the bisulfite treated DNA reveals the locations where the bisulfite treatment modified a base and, thus, reveals the locations of the cytosine residues within the initial M6 construct. Such a technique is very advantageous considering that, without modification, the currents for cytosine and guanine are often very similar making the different residue nearly indistinguishable. Once the cytosine residues are converted to uracil residues, the observed differences in current levels from an unconverted analyte can be associated with the location of cytosine residues in the original sequence (see FIG. 2).

The following is a description of strategies to selectively convert target nucleic acid residues into abasic positions to facilitate sequencing of the polymer in a nanopore based system.

It is demonstrated above that the conversion of a cytosine residue in an ssDNA polymer into a uracil residue facilitates the discrimination between cytosine and guanine residues, and ultimately assists in the mapping of all such residues in the sequence of the ssDNA polymer. An additional strategy is to selectively create abasic residues in place of specific target polymer subunits. This strategy can have the advantage of resulting in even greater signal changes using most nanopore systems. When abasic positions create new, unique signals that do not overlap with any potential subunit types in the polymer, the position of the abasic unit (and the original target subunit(s)) can be inferred without comparison of the signal to a reference. For nucleic acid polymers, the underlying approach is to re-encode the subunit base-type of interest (e.g. cytosine or guanine) with a modified base that can be recognized by a DNA repair enzyme that will excise the modified base leaving an abasic site. In this manner, the original base is converted to an abasic site, which will provide unique signal in a nanopore system. It is noted, however, that if the modification itself provides a unique signal, such as a cytosine to uracil modification as described above, no further modification is necessary before analysis in the nanopore system. However, if the signal changes are not large, or overlap to a degree with a signal corresponding to any other subunits, a comparison to a reference signal might be required to confirm the position of the modified bases.

DNA glycosylases are a major family of repair enzymes that can be exploited for the ultimate conversion of modified nucleic acid bases to abasic sites. Specific examples of DNA glycosylases that can act upon different base types and modifications are given below. As stated in the Parikh, S. S., et al., "Base excision repair enzyme family portrait: integrating the structure and chemistry of an entire DNA repair pathway," *Structure* 5(12):1543-1550 (1997), DNA glycosylases fall into two categories: "pure" glycosylases and AP (apurinic/apyrimidinic) lyase/glycosylases. The pure glycosylases leave an abasic site in the DNA, whereas the AP lyase/glycosylases leave an AP site with a nick that would cause a single strand of DNA to break. For many applications of this method, the use of pure glycosylases is preferred. As is well-known, there is considerable overlap in glycosylases, in that a single enzyme may recognize and remove numerous types of modified bases.

In a first strategy, bisulfite can be used to convert cytosine residues to uracil residues. As described above. This treatment can be followed by treatment with an error correction enzyme such as UDG, which is a pure glycosylase. This results in the conversion of the uracil residues now present in the nucleic acid into abasic sites. See Parikh et al., "Base excision repair enzyme family portrait: integrating the structure and chemistry of an entire DNA repair pathway," *Structure* 5(12):1543-1550 (1997), incorporated herein by reference in its entirety.

In a second strategy, the cytosine residues in a nucleic acid polymer can be replaced with modified cytosines, such as 5-methylcytosine. This can be accomplished by performing PCR or primer extension reactions using a polymerase with the proper dNTP mix that has dC replaced with the modified versions, such as 5-methyl-dCTP. The resulting DNA template can be exposed to a DNA correction enzyme, such as 5-methylcytosine DNA glycosylase, to remove 5-methylcytosine bases. See, e.g., Brooks, S. C., et al., "5-methylcytosine recognition by *Arabidopsis thaliana* DNA glycosylases DEMETER and DML3," *Biochemistry* 53(15):2525-2532 (2014) and Jang, H., et al., "Excision of 5-hydroxymethylcytosine by DEMETER family DNA glycosylases," *Biochem Biophys Res Commun.* 446(4):1067-1072 (2014), each incorporated herein by reference in their entireties, which describe the related DNA glycosylase enzymes DME, ROS1 and DML that recognize 5-methylcytosine and excise it to form an abasic site.

In a third strategy, the guanine residues in a nucleic acid polymer can be replaced with modified guanines, such as 7-methylguanine. This can be accomplished by performing PCR or primer extension reactions using a polymerase with the proper dNTP mix that has dG substituted with 7-methyl-dGTP. The resulting DNA template can be exposed to a DNA correction enzyme, such as *E. coli* alkA to remove the 7-methylguanine bases. See, e.g., Parikh, S. S., et al., "Base excision repair enzyme family portrait: integrating the structure and chemistry of an entire DNA repair pathway," *Structure* 5(12):1543-1550 (1997), incorporated herein by reference in its entirety, which describes that AlkA removes 7-methylguanine, and several other aberrantly methylated bases including 3-methyl adenine.

In a fourth strategy, the guanine residues in a nucleic acid polymer can be replaced with modified guanines, such as 3-methylguanine. This can be accomplished by performing PCR or primer extension reactions using a polymerase with the proper dNTP mix that has dG substituted with 3-methyl-dGTP. The resulting DNA template can be exposed to a DNA correction enzyme, such as alkA (from *E. coli*), tag (also referred to as "3-methyladenine DNA glycosylase I", from *E. coli*), MAG (from *S. cerevisiae*), MPG (from *M. musculus* or *H. sapiens*). See, e.g., Bjelland, S., et al., "Excision of 3-methylguanine from alkylated DNA by 3-methyladenine DNA glycosylase I of *Escherichia coli*," *Nucleic Acids Res.* 21(9):2045-2049 (1993), incorporated herein by reference in its entirety. Bjelland, S., et al., describes that *E. coli* alkA will efficiently remove 3-methyl guanine. To a lesser extent, the *E. coli* "tag" enzyme will also remove 3-methyl guanine. Both alkA and tag will efficiently remove 3-methyl-adenine, which can be useful in nanopores that result in nucleic acid signals where the adenine signal overlaps with any of the thymine, guanine, or cytosine signals. See also, Bjørås, M., et al., "Purification and properties of the alkylation repair DNA glycosylase encoded the MAG gene from *Saccharomyces cerevisiae*," *Biochemistry* 34(14):4577-4582 (1995), incorporated herein by reference in its entirety. Bjørås, M., et al. describes that the MAG gene of *S. cerevisiae* encodes an alkylation repair DNA glycosylase whose sequence is homologous to the alkA DNA glycosylase from *E. coli*. MAG was as effective as alkA in removing 3-methyladenine, 7-methylguanine, and 7-methyladenine. 3-methylguanine was excised 20-40 times more slowly by MAG than by alkA. The kinetics of 3-methylguanine excision by MAG were found to be similar to the low rate of 3-methylguanine excision catalyzed by 3-methyladenine DNA glycosylase I (tag) of *E. coli*. See also, Roy, R., et al., "Distinct substrate preference of human and mouse N-methylpurine-DNA glycosylases," *Carcinogenesis* 17(10):2177-2182 (1996), incorporated herein by reference in its entirety. Roy, R., et al. discloses that mouse MPG removes 7-methylguanine and 3-methylguanine at a ~2- to 3-fold higher rate than the human protein when adjusted for equal activity for the release of 3-methyladenine from DNA.

Accordingly, a variety of known nucleic acid error detection enzymes can be employed to convert modified nucleic acid monomeric subunits into abasic residues. This activity can be leveraged into the present method by implementing rational modifications in a nucleic acid sequence to create targets for the error detection enzymes. The modifications do not require a priori knowledge of the locations (or even initial presence) of the target nucleic acid monomeric subunits. The described strategies result in abasic sites corresponding to the sites of any of the target nucleic acid monomeric subunits, and thus will produce readily identifiable signals in a nanopore system that can be used to readily and unambiguously identify the locations of the initial target nucleic acid monomeric subunits in the initial nucleic acid sequence.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for analyzing a polymer analyte, comprising:
   (a) selectively modifying a target polymer subunit of a kind in a pre-analyte polymer to produce a polymer analyte with an abasic site, wherein selectively modifying the target polymer subunit of a kind comprises contacting the target polymer subunit of a kind with an agent to produce a modified subunit and converting the modified subunit to an abasic site;
   (b) translocating the polymer analyte comprising the abasic site from a first conductive liquid medium to a second conductive liquid medium through a nanopore, wherein the nanopore provides liquid communication between the first conductive liquid medium and the second conductive liquid medium;
   (c) measuring an ion current between the first conductive liquid medium and the second conductive liquid medium as the polymer analyte passes through the nanopore; and (d) detecting the abasic site based on the measured ion current.

2. The method of claim 1, wherein step (a) further comprises selectively modifying a plurality of a target polymer subunits of the same kind in the pre-analyte polymer.

3. The method of claim 2, wherein the pre-analyte polymer comprises a nucleic acid, a DNA, an RNA; a PNA; a polypeptide; or a combination thereof.

4. The method of claim 3, wherein the kind of target polymer subunit is a cytosine residue, a guanine residue, a thymine residue, an adenine residue, or a uracil residue.

5. The method of claim 4, wherein selectively modifying the cytosine residue comprises selectively converting the cytosine residue into a uracil residue.

6. The method of claim 5, wherein converting the cytosine residue into the uracil residue comprises contacting the pre-analyte polymer with an agent selected from bisulfite, cytosine deaminase, NO, $N_2O_3$, and Echinomycin.

7. The method of claim 5, wherein selectively modifying the cytosine residue further comprises converting the uracil residue into an abasic site, thereby producing the polymer analyte.

8. The method of claim 7, wherein converting the uracil residue into an abasic site comprises contacting the pre-analyte polymer with a nucleic acid error correction enzyme.

9. The method of claim 8, wherein the nucleic acid error correction enzyme is uracil deglycosylase (UNG).

10. The method of claim 4, wherein either the kind of target polymer subunit is a cytosine residue and selectively modifying the cytosine residue comprises selectively methylating the cytosine residue, or the kind of polymer subunit is a guanine residue and selectively modifying the guanine residue comprises selectively methylating the guanine residue.

11. The method of claim 10, wherein selectively methylating the cytosine residue comprises contacting the pre-analyte polymer with a methyltransferase enzyme.

12. The method of claim 10, wherein selectively modifying the cytosine residue or guanine residue further comprises converting the methylated cytosine residue into an abasic site, thereby producing the polymer analyte.

13. The method of claim 2, wherein step (d) comprises:
(i) comparing the measured ion current to an ion current corresponding to a reference polymer comprising the same sequence as the analyte polymer wherein the subunit of a kind in the reference polymer is not modified; and
(ii) detecting the presence or absence of a difference in the ion currents compared in step (i), wherein the presence or absence of a difference in ion currents indicates the presence or absence of the subunit modification in the polymer analyte, respectively.

14. The method of claim 13, further comprising translocating the reference polymer from the first conductive liquid medium to the second conductive liquid medium through the nanopore and measuring an ion current to provide the ion current corresponding to the reference polymer.

15. The method of claim 1, further comprising determining the position of the abasic site in the polymer analyte based on a characteristic of the measured ion current.

16. The method of claim 15, comprising determining the identity of the target polymer subunit at a position in the pre-analyte polymer sequence that corresponds to the position of the modified subunit in the polymer analyte.

17. The method of claim 2, further comprising:
performing the steps (a) through (c) for a plurality of pre-analyte polymers that comprise a common sequence;
producing a consensus map of the plurality of ion currents measured in step (c); and
detecting the presence of multiple modified subunits in the common sequence.

18. A method for analyzing a nucleic acid analyte, comprising:
(a) incorporating a modified nucleobase into the nucleic acid analyte;
(b) contacting the nucleic acid analyte with an error correction enzyme capable of removing the modified nucleobase to provide an abasic site in the nucleic acid analyte;
(c) translocating the nucleic acid analyte from a first conductive liquid medium to a second conductive liquid medium through a nanopore, wherein the nanopore provides liquid communication between the first conductive liquid medium and the second conductive liquid medium;
(d) measuring an ion current between the first conductive liquid medium and the second conductive liquid medium as the nucleic acid analyte passes through the nanopore; and
(e) detecting the abasic site based on the measured ion current.

* * * * *

UNITED STATES PATENT AND TRADEMARK OFFICE
CERTIFICATE OF CORRECTION

| | |
|---|---|
| PATENT NO. | : 10,017,814 B2 |
| APPLICATION NO. | : 14/915611 |
| DATED | : July 10, 2018 |
| INVENTOR(S) | : Jens H. Gundlach |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 209 days.

Signed and Sealed this
Thirteenth Day of December, 2022

Katherine Kelly Vidal
*Director of the United States Patent and Trademark Office*